US00PP37495P2

(12) United States Plant Patent
Jarnagin

(10) Patent No.: US PP37,495 P2
(45) Date of Patent: Jun. 30, 2026

(54) ***SAMBUCUS* PLANT NAMED 'Æ-1'**

(50) Latin Name: ***Sambucus canadensis* L.**
Varietal Denomination: ***Æ*-1**

(71) Applicant: Hyldemoer & Company, LLC, Chiefland, FL (US)

(72) Inventor: Dave Jarnagin, Williston, FL (US)

(73) Assignee: Hyldemoer & Company, LLC, Chiefland, FL (US)

( * ) Notice: Subject to any disclaimer, the term of this patent is extended or adjusted under 35 U.S.C. 154(b) by 0 days.

(21) Appl. No.: 19/065,369

(22) Filed: Feb. 27, 2025

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226, 156
CPC ..... A01H 5/02; A01H 5/00; A01H 5/08
See application file for complete search history.

(56) References Cited

U.S. PATENT DOCUMENTS

| | | | |
|---|---|---|---|
| PP10,675 | P | 11/1998 | Lyrene |
| PP12,305 | P2 | 12/2001 | Tobutt |
| PP15,575 | P2 | 2/2005 | Tobutt |
| PP23,633 | P2 | 5/2013 | Tobutt |
| PP26,425 | P2 | 2/2016 | Walmsley et al. |
| PP26,613 | P2 | 4/2016 | Wood |
| PP28,314 | P3 | 8/2017 | Brand |
| PP28,957 | P2 | 2/2018 | Boer |
| PP29,051 | P3 | 3/2018 | Tobutt et al. |
| PP35,979 | P3 | 7/2024 | Jones et al. |

*Primary Examiner* — Kent L Bell

(74) *Attorney, Agent, or Firm* — Koenig IP Works, PLLC; Katherine Koenig

(57) ABSTRACT

A new and distinct cultivar of *Sambucus* plant named 'Æ-1', characterized by reliable fruit set, low chill requirement, early and even ripening, short harvest period, and high-quality fruit characteristics. The plant is self-compatible, producing abundant, medium to medium-large fruit after self-pollination, with high concentrations of specific anthocyanins. Additionally, 'Æ-1' is particularly suitable for large-scale, commercial production centered in North-Central Florida.

12 Drawing Sheets

Genus and species: *Sambucus canadensis* L. (*Sambucus nigra* subspecies *canadensis* R. BOLLI).
Cultivar denomination: 'Æ-1'.

CROSS-REFERENCE TO RELATED APPLICATIONS

N/A.

BACKGROUND OF THE NEW CULTIVAR

The present invention relates to a new and distinct cultivar of *Sambucus*, botanically known as *Sambucus canadensis* L. (also known as *Sambucus nigra* subspecies *canadensis* R. BOLLI), and hereinafter referred to by the name 'Æ-1'. *Sambucus canadensis* is a member of the family Viburnaceae.

The *Sambucus* plant described herein belongs to the species *Sambucus canadensis*. Ongoing taxonomic updates within the genus alternatively classify this species as *Sambucus canadensis* or *Sambucus nigra* subspecies *canadensis*. The genus, currently placed in the family Viburnaceae, was historically classified under the family Caprifoliaceae until 1994 and more recently under Adoxaceae.

The new cultivar 'Æ-1' represents the early achievements of a planned breeding program aimed at developing *Sambucus* cultivars optimized for production in warm climates, particularly in the southeastern United States, including Florida's blueberry-growing regions. The breeding program focuses on creating low-chill *Sambucus* cultivars to provide Southeastern growers with a commercially viable, high-value crop option. These cultivars can diversify the agricultural economy by offering a new commodity for growers operating at various scales. Moreover, early-ripening *Sambucus* cultivars like 'Æ-1' could secure premium prices by entering the market ahead of crops from established production areas in Europe and the U.S. Midwest. Such cultivars can also enhance the selection of fruit-bearing plants available to home gardeners.

The anthocyanin-rich juice and pomace derived from fruit of 'Æ-1' offer significant commercial value, aligning with the global market's increasing focus on high-anthocyanin crops. The option to incorporate *Sambucus* into existing production schedules could also enhance labor efficiency during seasonal lulls, avoiding labor displacement while minimizing overlap with other major commodities. For instance, production of 'Æ-1' fits into a harvest sequence starting with blueberry, followed by blackberry, 'Æ-1' *Sambucus*, and concluding with muscadine grape harvest.

The breeding program's objectives include developing cultivars with high anthocyanin content, uniform and reliable early ripening, and the capacity for both commercial-scale production and small-scale home cultivation. The resulting cultivar, 'Æ-1', satisfies these goals, demonstrating exceptional adaptability to warm climates, including regions with low chill hour accumulations over winter. Additionally, the program seeks to develop cultivars with edible flowers for use in various products, especially beverages. 'Æ-1' produces aromatic, edible flowers.

The new cultivar 'Æ-1' originated as a seedling from an open pollination where 'JLAV5-1' (unpatented) is the seed parent. The open pollination occurred in a field setting containing 86 genotypes of *S. canadensis* at a commercial production site in Chiefland, Florida, in 2021. The pollen parent is unknown. The seedling was identified in a high-density, container nursery and subsequently transplanted as a trimmed central root section into a plot adjacent to its seed parent's location. Propagation (asexual reproduction) of 'Æ-1' was conducted using hardwood cuttings collected from the Chiefland, Florida site in fall of 2022, fall of 2023, and summer of 2024, and then asexually reproduced and cultivated in both Chiefland, Florida and Williston, Florida in all three years. Asexual reproduction of 'Æ-1' via hardwood cuttings consistently demonstrated its unique traits, confirming their stability and reproducibility across successive generations.

The new cultivar 'Æ-1' was evaluated in multiple Certified Naturally Grown test plots in Chiefland and Williston, Florida, during 2023 and 2024. Observations revealed its reliable fruit set, early ripening, and high-quality fruit characteristics. The plant is self-compatible, producing abundant, medium-large fruit after self-pollination, with high concentrations of distinct anthocyanins verified through chemical analyses conducted between 2022 and 2024. While 'Æ-1' exhibits typical susceptibility to *P. wisconsinensis* (eriophyid mite), its early fruiting minimizes losses caused by this pest pressure.

Plant Breeder's Rights for this cultivar have not been applied for. The new *Sambucus* cultivar 'Æ-1' has not been made publicly available more than one year prior to the filing of this application.

SUMMARY OF THE INVENTION

The new *Sambucus* cultivar 'Æ-1' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'Æ-1' represents a novel advancement in *S. canadensis*, specifically designed for agricultural production as a commodity crop. Unlike previously patented *Sambucus* cultivars, which have been primarily developed for ornamental purposes (e.g., *S. nigra* and *S. racemosa*), 'Æ-1' is optimized for large-scale production.

The new cultivar 'Æ-1' combines low chill requirement, early fruit ripening, a short harvest period, even ripening, and concentrated levels of specific anthocyanins in a cultivar intended for large scale production capability.

This cultivar is specifically comparable to the development of early southern highbush blueberry cultivars, such as 'Star' (U.S. Plant Pat. No. 10,675P), which transformed blueberry production in the southeastern U.S. Similarly, 'Æ-1' performs reliably as far south as Williston, Florida, with the earliest ripening of all varieties trialed to date following standardized crop production practices for *S. canadensis*.

Ongoing field trials toward development of a commercially viable *Sambucus* cultivar, uniquely suited for regions with mild winters and low chill hour accumulations, were utilized in the evaluation of 'Æ-1'. This cultivar's distinctive horticultural traits make it advantageous for production in such climates.

The following traits have been repeatedly observed and are determined to be the unique characteristics of the new *Sambucus* cultivar. These characteristics in combination distinguish 'Æ-1' as a new and distinct cultivar of *Sambucus:*

1. Early precocity: This new cultivar establishes rapidly, producing marketable flowers and fruit in its establishment year. It demonstrates exceptional adaptability to a climate with a mean coldest-month temperature of 13° C. and low chill hour accumulations (less than 400 units annually in 9 of 10 winters, 2014-2023).
2. Rapid productivity: When propagated by hardwood cuttings planted directly in rows in early December, the cultivar exhibits rapid growth, a semi-erect and semi-dwarf habit, and suitability for high-density planting systems.
3. Annual coppicing adaptability: Following annual coppicing (cutting near to ground level) at the end of the growing season, the plant demonstrates vigorous regrowth, maintaining consistent productivity.
4. Primocane fruit production: The cultivar reliably produces ripe fruit on primocanes 50 to 60 days after flowering in North-Central Florida
5. Consistent ripening window: Fruit ripening is highly reliable, with 60% of cymes ripening between June 30 and July 10 and 90% of the crop ripening by July 20 in North-Central Florida.
6. Extended harvest potential: The new cultivar produces 2-4 auxiliary cymes per primocane between July 15 and August 31, emanating from 2-6 primocanes in the establishment year and increasing annually in number of primocanes produced.
7. Fruit quality: The new cultivar produces medium to medium-large berries, with relatively uniform ripening across the cyme.
8. Juice quality: Juice of the new cultivar exhibits high anthocyanin concentrations, including a significant proportion of acylated anthocyanin compounds, offering extended shelf stability compared to the non-acylated anthocyanins produced by *S. nigra*, exclusively.
9. Disease resistance: The new cultivar demonstrates high resistance to fungal and bacterial leaf-spot diseases, including Cercospora, ensuring reliable production across trial locations.
10. Pest management: While susceptible to *P. wisconsinensis* (eriophyid mites), flowers of the new cultivar form early enough, and fruit ripens quickly enough to minimize crop losses from infestation of this common *Sambucus* plant pest.
11. Propagation: The new cultivar is readily propagated via hardwood cuttings, with an average of 15-30 viable cuttings per plant being produced at the end of the establishment year following coppicing in November-December, or as early as August, with 100% viability of hardwood cuttings in all field trials.
12. High-density planting: The new cultivar is successfully cultivated at densities ranging from 900 to 7,200 plants per acre, depending on the grower's intended cropping system.

The new cultivar 'Æ-1' differs from other previously patented *Sambucus* cultivars in that it is mainly intended for agricultural production as a commodity crop, as compared to the ornamental characteristics noted for all previously patented *Sambucus* cultivars of the species *S. nigra* and *S. racemosa* (for example, 'Gerda' (U.S. Plant Pat. No. 12,305P2), 'Eva' (U.S. Plant Pat. No. 15,575P2), 'Eiffel 1' (U.S. Plant Pat. No. 23,633P2), 'WALFINB' (U.S. Plant Pat. No. 26,425P2), 'SMNSRD4' (U.S. Plant Pat. No. 26,613P2), 'SNR1292' (U.S. Plant Pat. No. 29,051P3), 'Jdeboer001' (U.S. Plant Pat. No. 28,957P2), 'SANIVALK' (U.S. Plant Pat. No. 28,314P3), and 'HYFJOLAIS' (U.S. Plant Pat. No. 35,979P3)).

Plants of the new *Sambucus* cultivar 'Æ-1' differ from plants of the female (seed) parent, 'JLAV5-1', in the following characteristics:

1. 'Æ-1' reliably produces ripe berries 7-10 days earlier than 'JLAV5-1' with 'JLAV5-1' being a relatively early producer itself.
2. 'Æ-1' is significantly shorter and more compact than 'JLAV5-1', with plants of 'JLAV5-1' typically being approximately 30% to approximately 50% taller and as much as twice as wide as those of 'Æ-1'.
3. 'Æ-1' produces significantly fewer non-bearing auxiliary branches compared to 'JLAV5-1'.

Plants of the new *Sambucus* cultivar 'Æ-1' can be compared to 'Gerda' (U.S. Plant Pat. No. 12,305P2) in the following characteristics:

1. 'Gerda' (currently and/or formerly commercially sold under the name BLACK BEAUTY™) is sold as an ornamental landscape plant. In contrast, 'Æ-1' is not primarily intended for sale as an ornamental landscape plant, but instead as a commercial, agricultural cultivar for food and botanical crop production at various scales.
2. 'Gerda' has very dark purple-red foliage, whereas 'Æ-1' has green foliage.
3. 'Gerda' has an intense pink flower coloration, whereas 'Æ-1' has creamy white flower coloration.

DESCRIPTION OF THE FIGURES

The accompanying photographs (as shown in FIGS. 1-12) illustrate the overall appearance of the new *Sambucus* cultivar 'Æ-1'. These photographs show the colors as true as can be reasonably obtained in colored reproductions of this type. Colors in the photographs may differ slightly from the color values cited in the detailed botanical description, which accurately describe the colors of the new cultivar.

DETAILED BOTANICAL DESCRIPTION OF THE CULTIVAR

Figure 1:
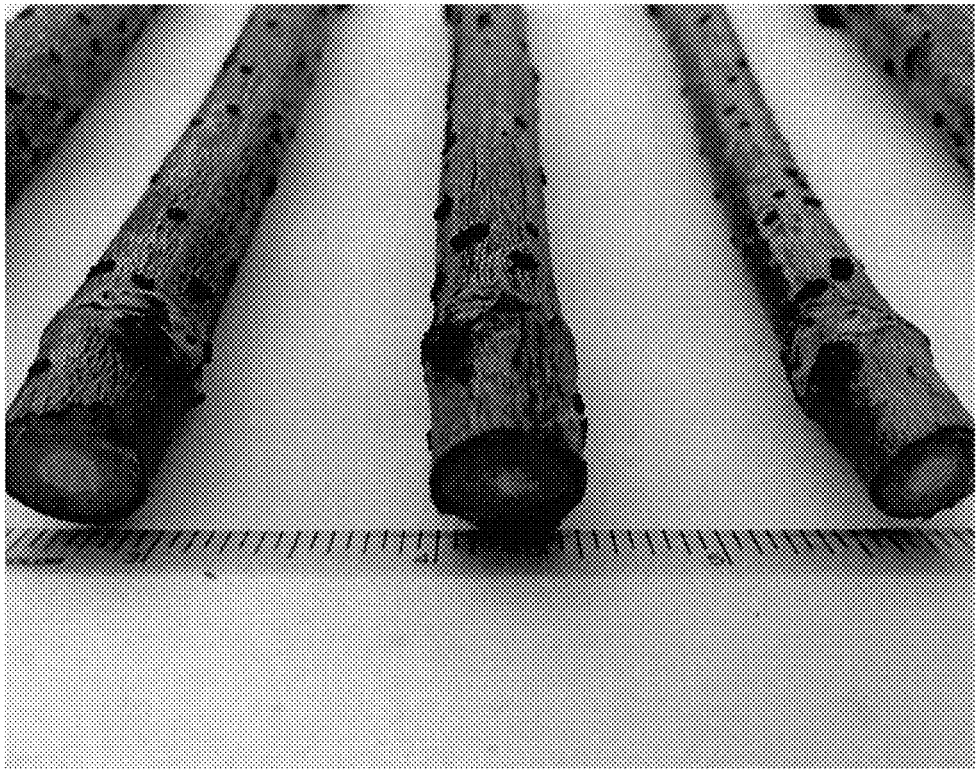
FIG. 1 shows nodal hardwood cuttings usable in asexual propagation of the new cultivar 'Æ-1', with a ruler shown for measurement.
Figure 2:
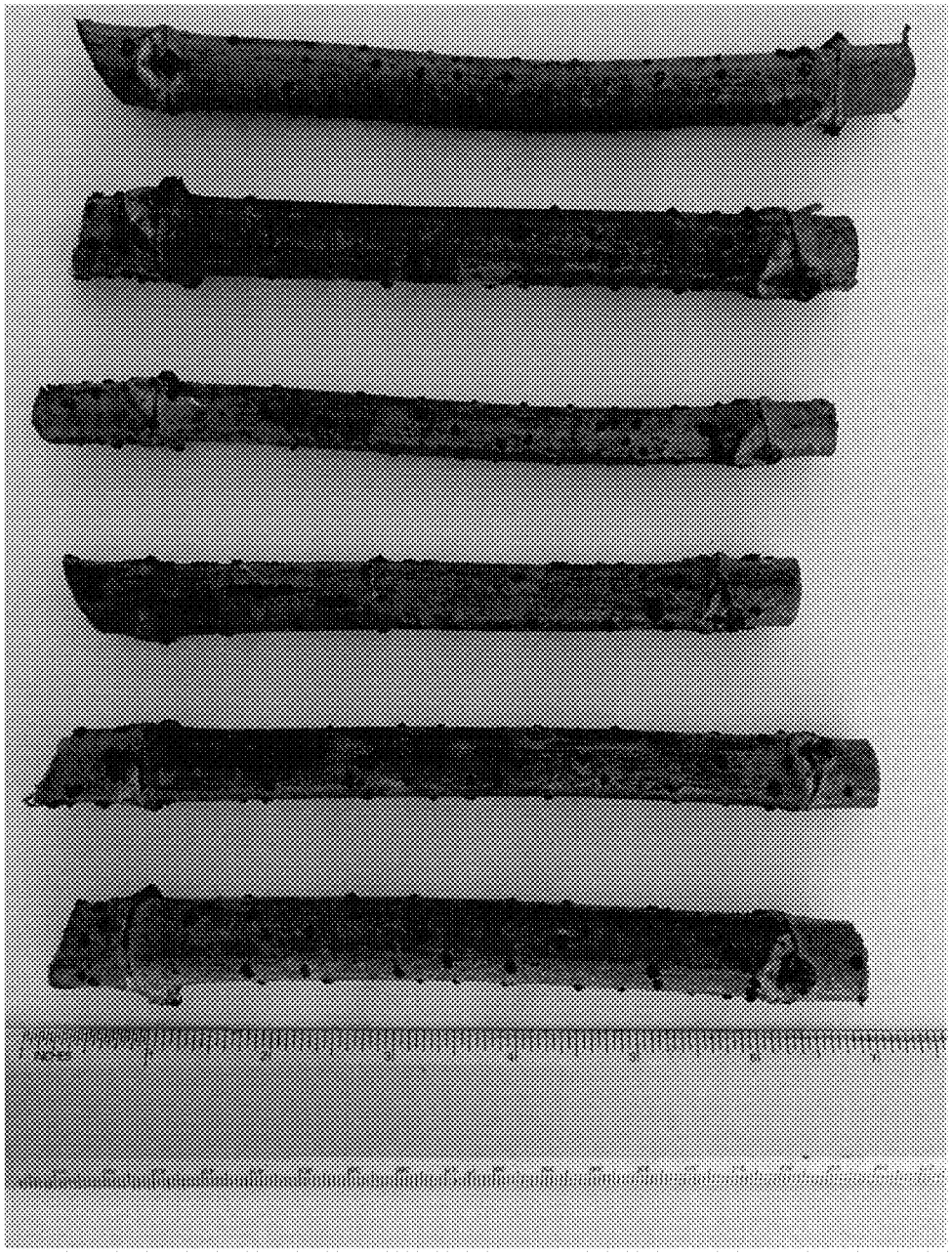
FIG. 2 shows length and proportions of nodal hardwood cuttings usable in asexual propagation of the new cultivar 'Æ-1', with a ruler shown for measurement.
Figure 3:
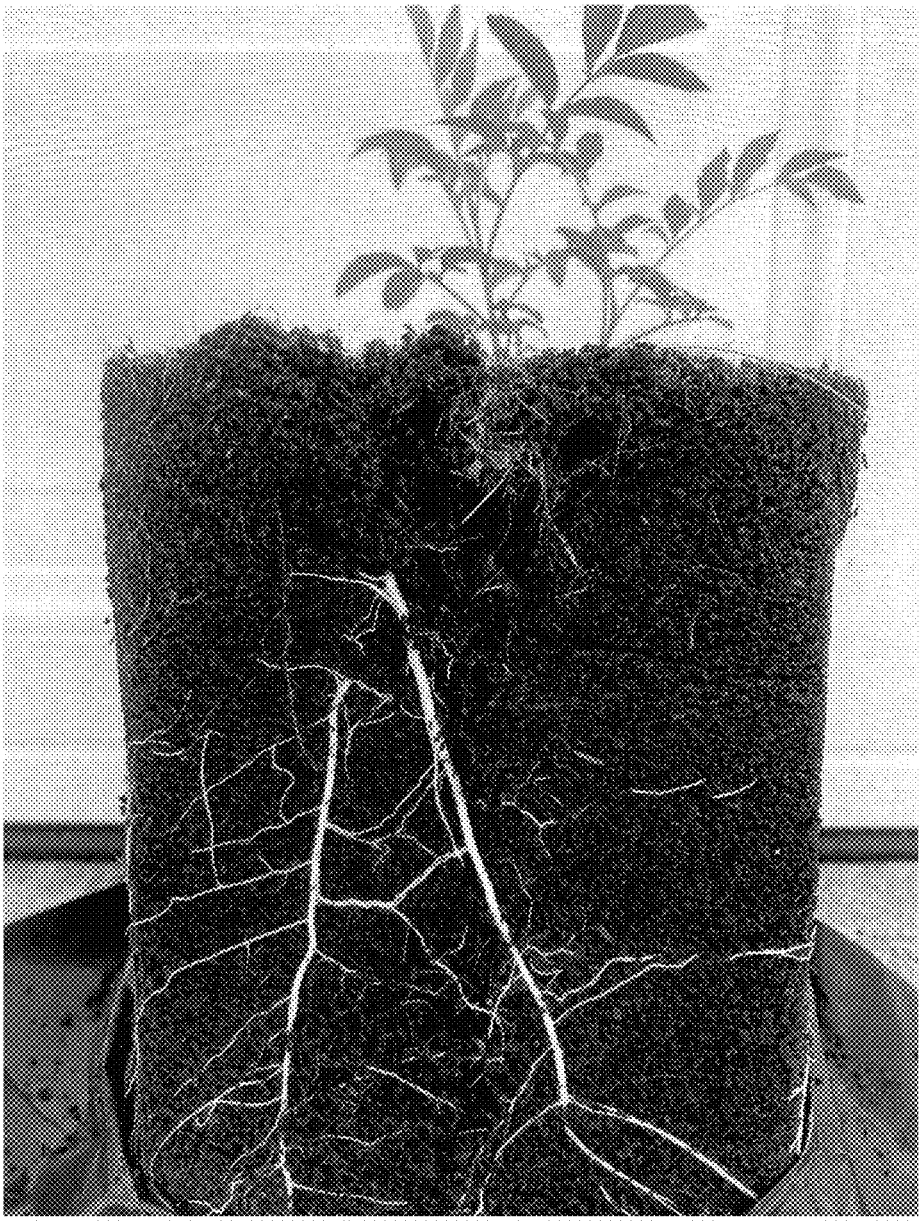
FIG. 3 shows the fibrous root system of a container-grown cutting of the new cultivar 'Æ-1', illustrating the rapid establishment of hardwood cuttings of the new cultivar. The root system development shown in FIG. 3 is at 40 days from planting.
Figure 4:
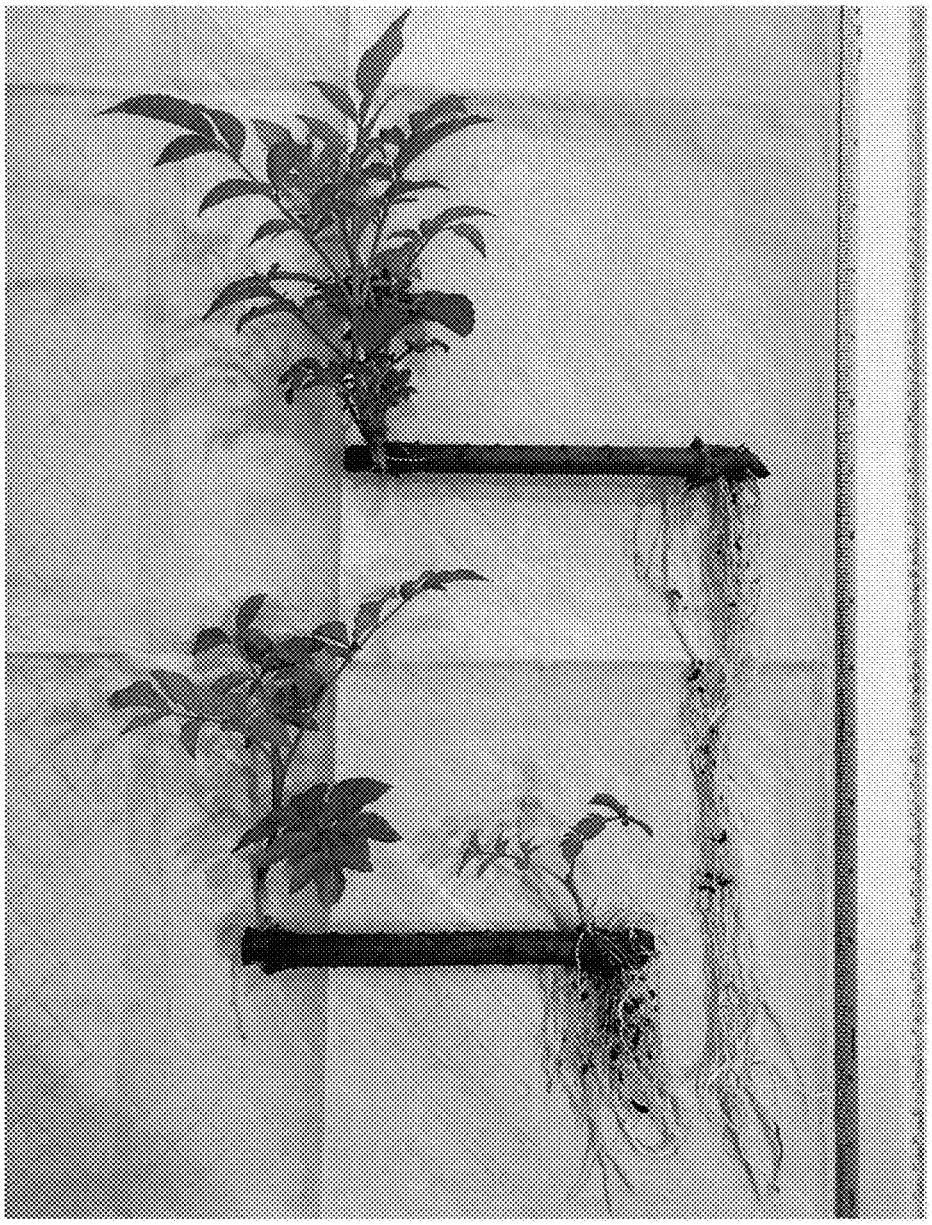
FIG. 4 shows the development of asexually reproduced plants of the new cultivar 'Æ-1' at 40 days from planting.
Figure 5:
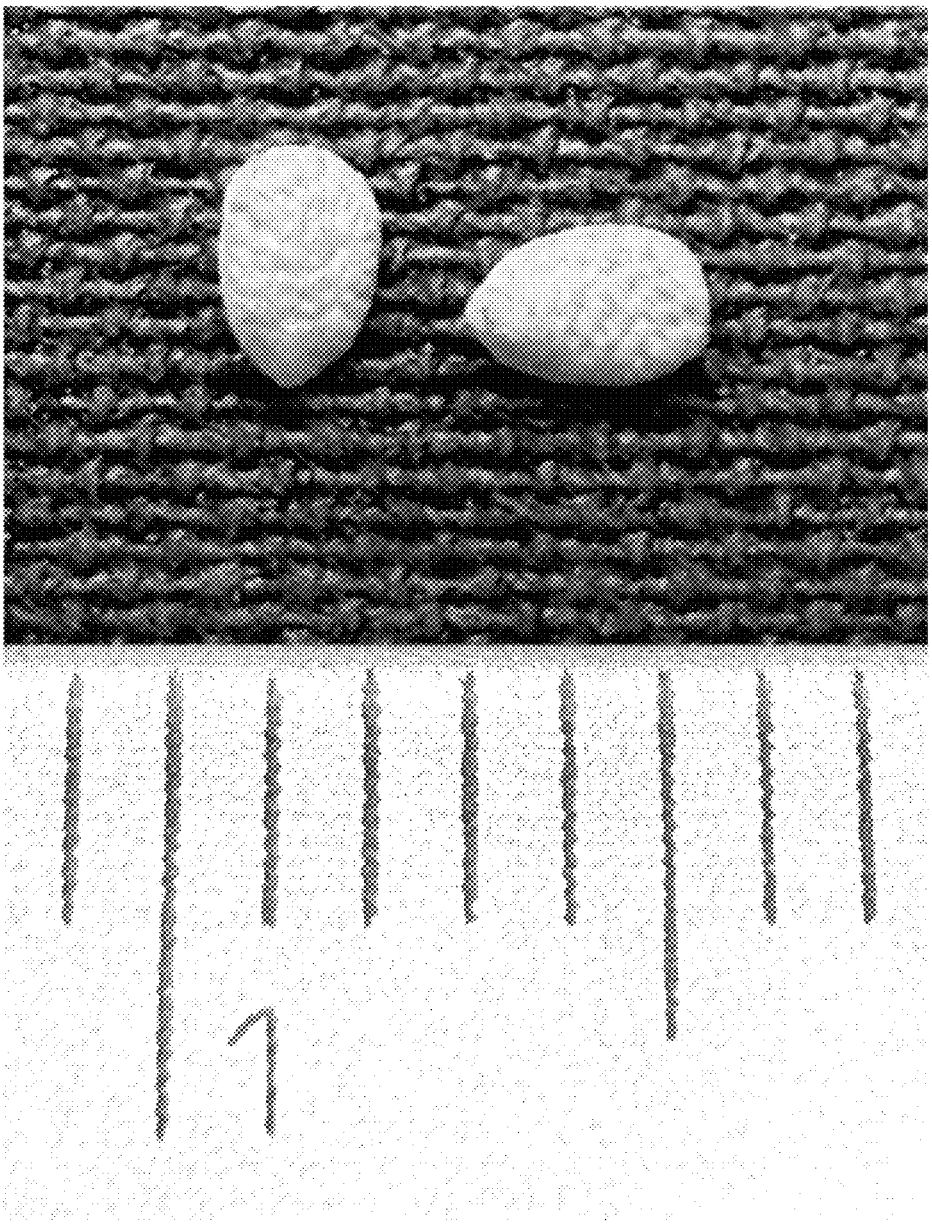
FIG. 5 shows a magnified view of seeds of the new cultivar 'Æ-1'.
Figure 6:
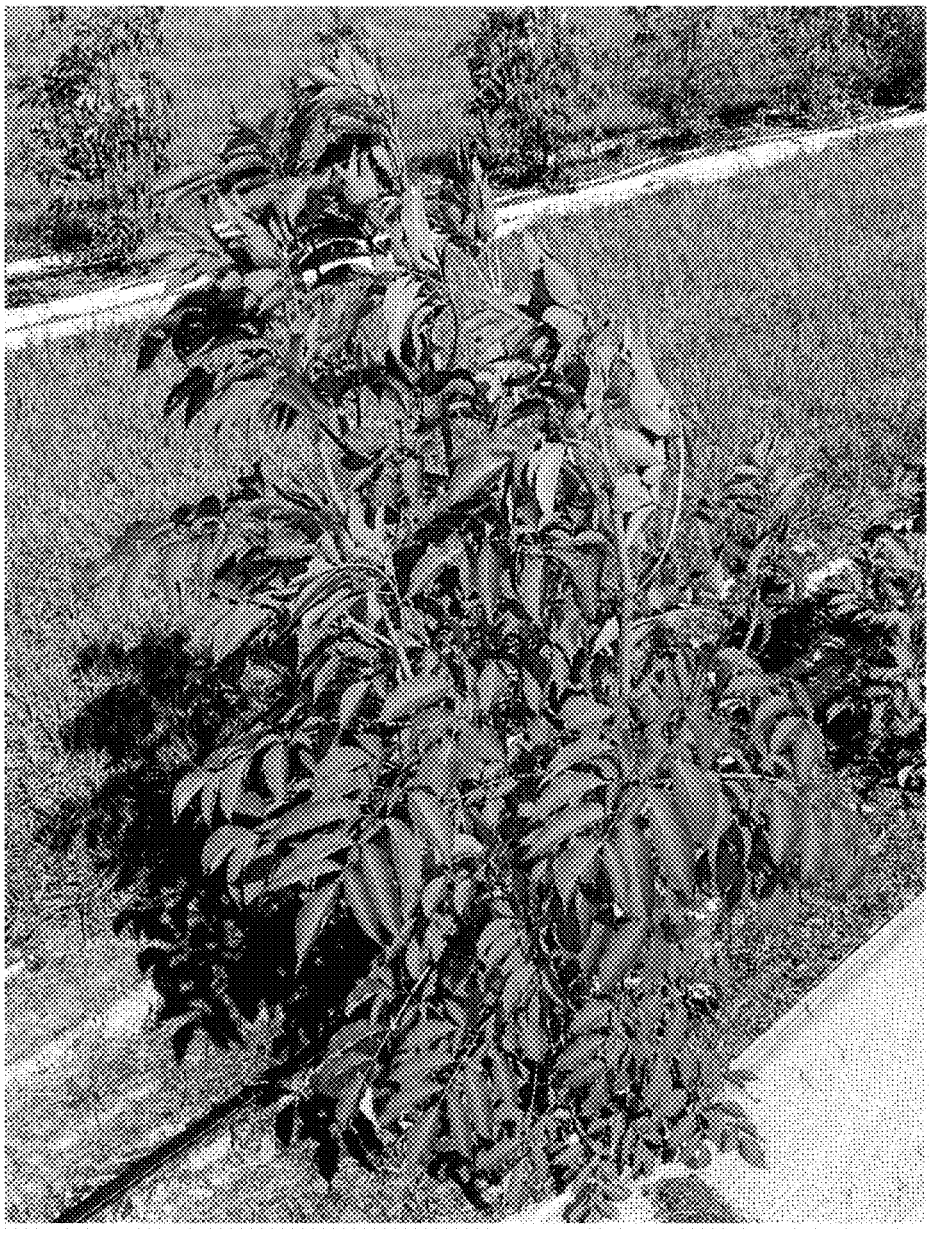
FIG. 6 shows the rate of annual regrowth of plants of the new cultivar 'Æ-1' at 130 days post-coppicing in winter in the plant's second year of growth.
Figure 7:
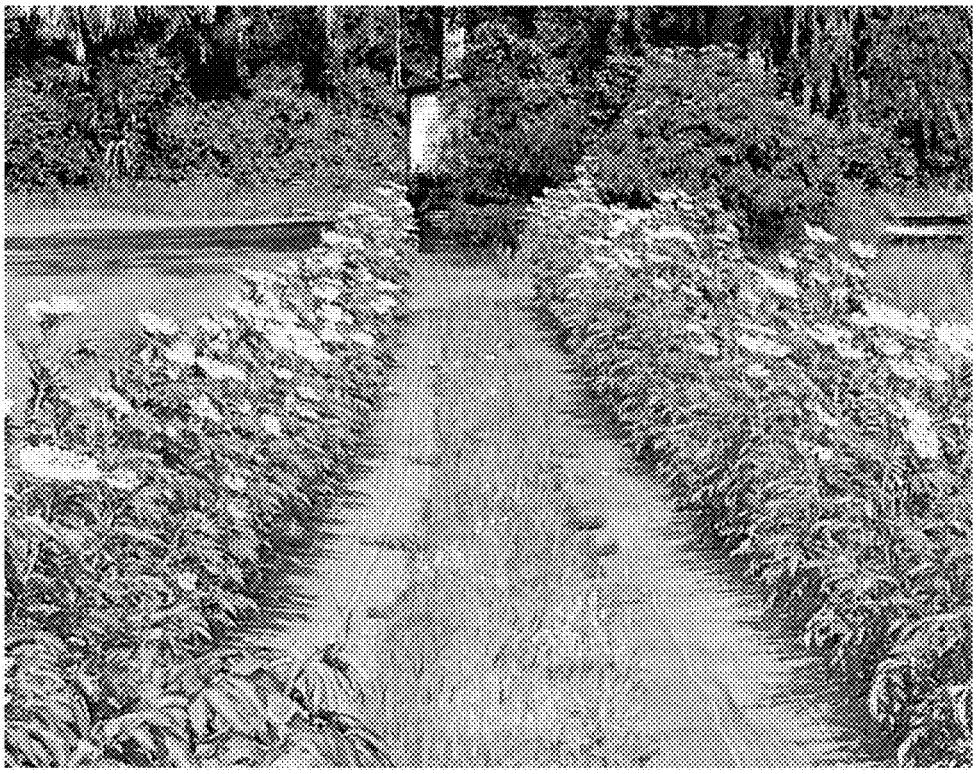
FIG. 7 shows establishment of plants of the new cultivar 'Æ-1' nearing full bloom of primocane flowering on May 9, 2024, at 150 days from planting of hardwood cuttings directly in-row.
Figure 8:
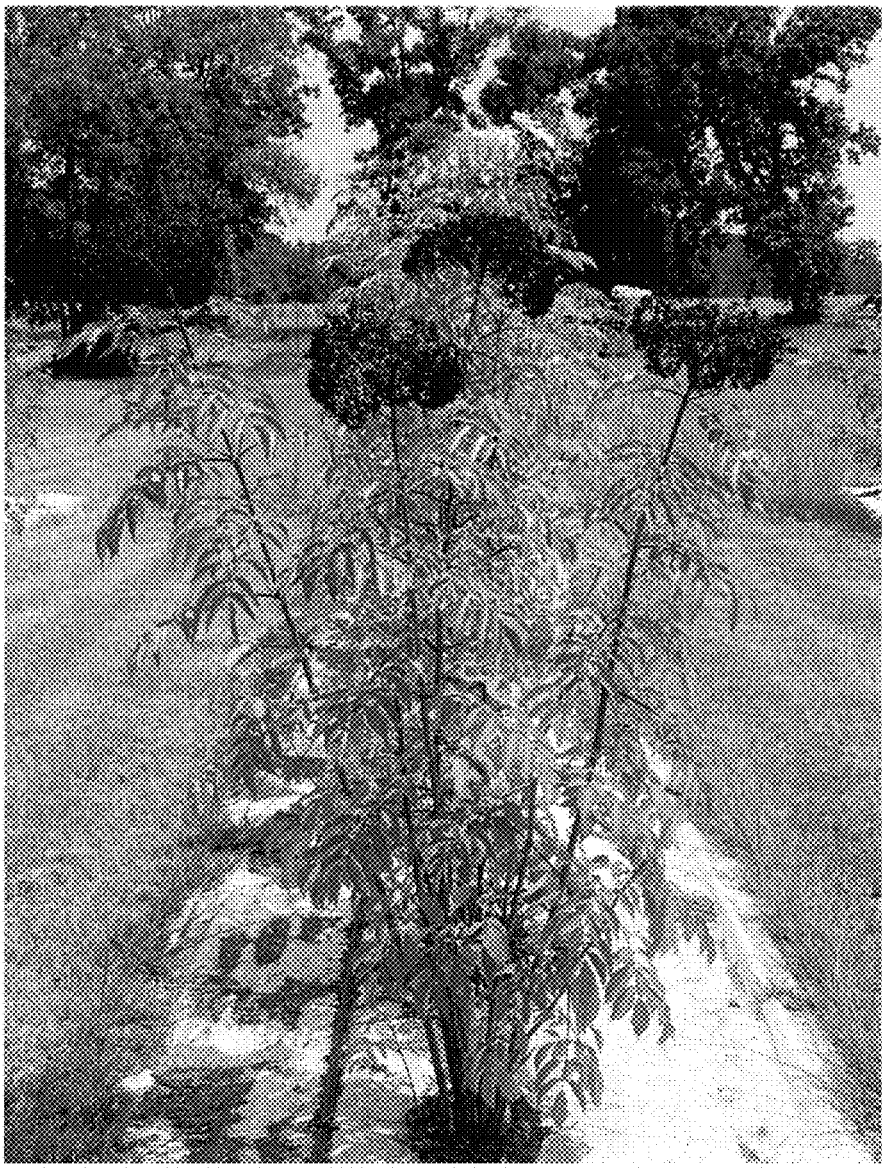
FIG. 8 shows the original seedling of the new cultivar 'Æ-1' at near full ripeness in its second season on Jun. 30, 2023.
Figure 9:
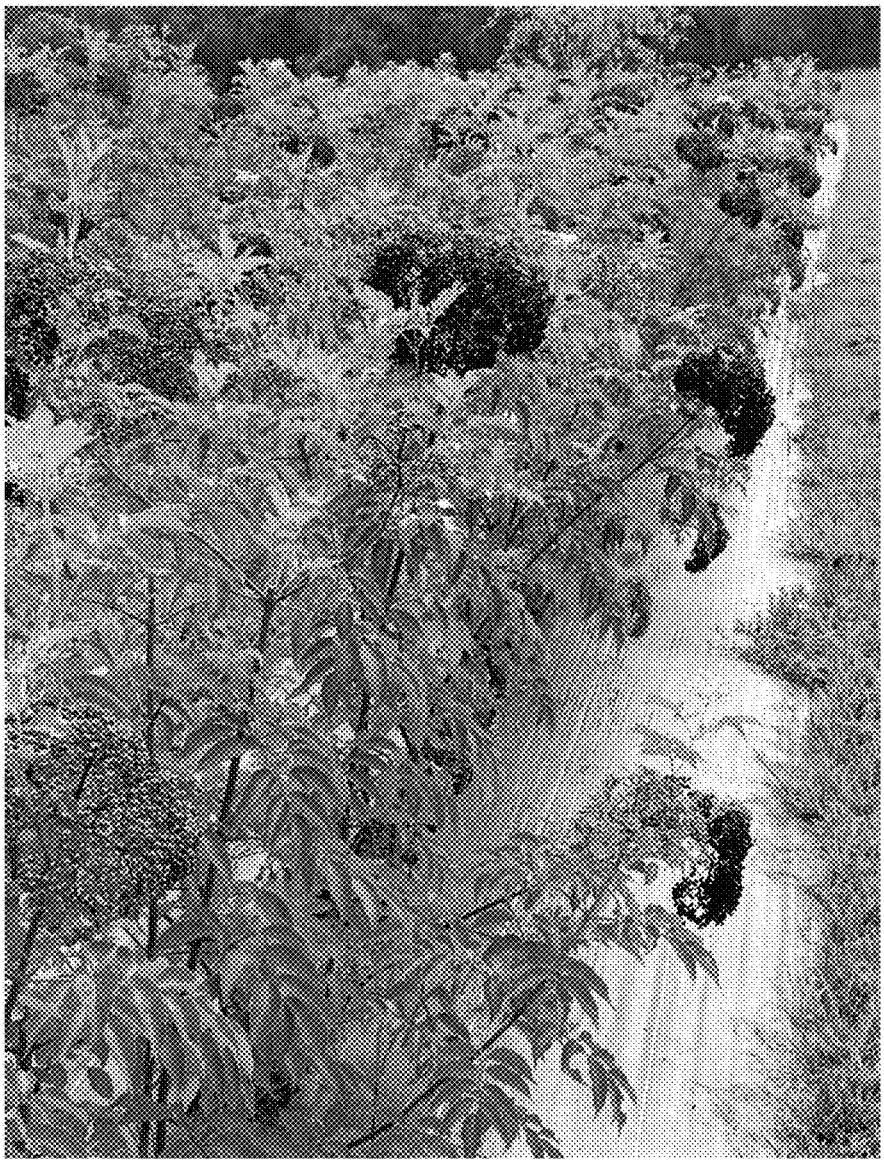
FIG. 9 shows establishment year plants of the new cultivar 'Æ-1' at the mid-point of harvest on Jul. 15, 2024, at 7 months from planting.
Figure 10:
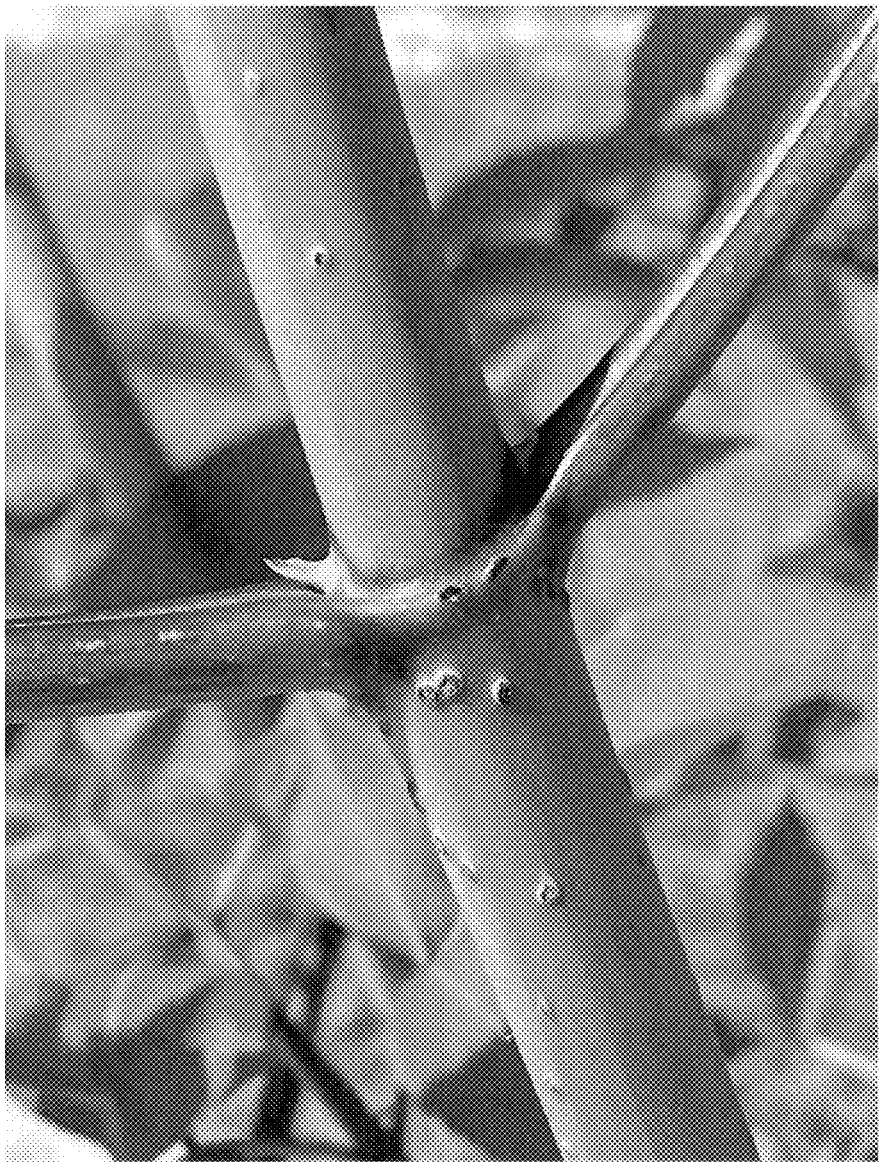
FIG. 10 shows the anthocyanin coloration of the node and petiole in the spring that is characteristic of the new cultivar 'Æ-1', prior to bloom in the plant's first year, and is typical of any age observed.
Figure 11:
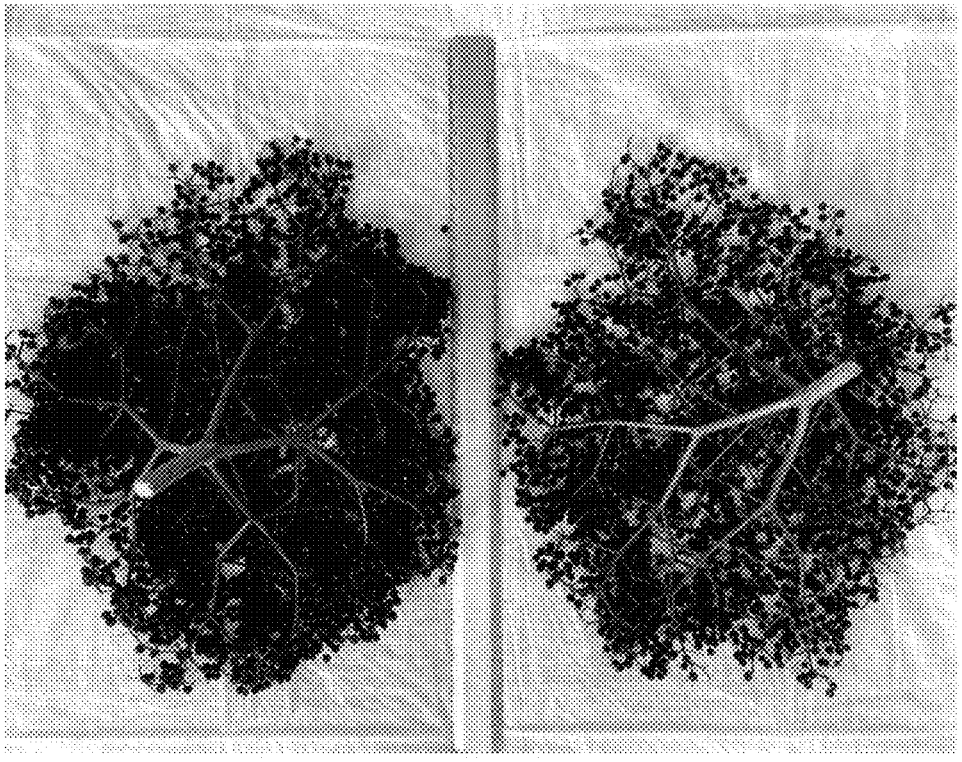
FIG. 11 shows evenness of ripening that is characteristic of larger-than-average fruit clusters of the new cultivar 'Æ-1' taken from a specimen in its second year, whereas evenness of ripening across the fruit cluster is typically best in smaller cymes.
Figure 12:
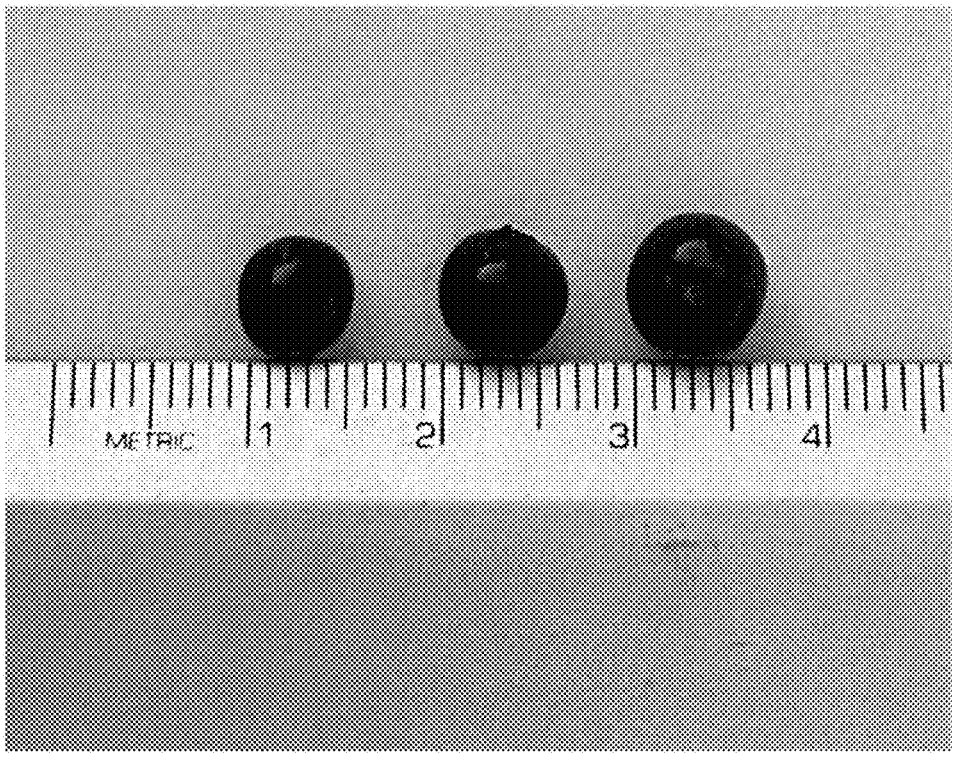
FIG. 12 shows the black color and size range of ripe berries that is characteristic of the new cultivar 'Æ-1' in the plant's first year, and is typical of any age observed.

The following descriptions outline the distinctive botanical characteristics of 'Æ-1'. Data were collected from observations conducted in Chiefland and Williston, Levy County, Florida, during the years 2022 through 2024. Variations in environmental, seasonal, climatic, and cultural conditions may influence these characteristics. Consequently, color designations, color descriptions, and other phenotypic traits may vary from the stated values. While 'Æ-1' has been evaluated in its primary trial locations, its potential cultivation range likely spans from the 26th parallel north through the species' natural range significantly further northward.

Observations and measurements were taken from plants in their establishment year through their third year of growth, with the indicated values representing averages derived from several specimens at their annual prime maturity. Color determinations reference the Pantone Color Formula Guide (ISBN 1-881509-81-8) and are matched to RGB hexadecimal values unless general color terminology of standard dictionary significance is used for accessibility. Additional descriptive terminology follows *Plant Identification Terminology: An Illustrated Glossary* (2nd edition, James G. Harris and Melinda Woolf Harris), unless otherwise defined.

BOTANICAL DESCRIPTION

Botanical classification:

*Family*.—Viburnaceae (formerly classified in Caprifoliaceae and Adoxaceae).

*Botanical name*.—*Sambucus canadensis* L. (Alternatively, *S. nigra* ssp. *canadensis* R. BOLLI).

*Common names*.—*Sambucus*, American *Sambucus*, North American black elderberry, American elderberry, elderberry, elderflower, elder.

*Cultivar*.—'Æ-1'.

Parentage:

*Female or seed parent*.—'JLAV5-1' (unpatented).

*Male or pollen parent*.—Unknown.

General:

*Propagation*.—Hardwood cuttings.

*Growth habit*.—Moderately upright (semi-erect).

*Height*.—170 cm on average.

*Width*.—110 cm on average.

*Precocity*.—High.

*Vigor*.—High.

*Self-fruitfulness*.—Self-fruitful.

*Cold hardiness*.—Observed to be hardy in USDA Zone 9. This species is documented to be hardy through USDA Zone 4.

*Cold tolerance*.—High, normal for the species.

*Chilling requirement*.—Comparatively very low for the species, estimated between 100 and 300 hours.

*Heat tolerance*.—Comparatively high resistance to heat for the species.

Resistance to pests and diseases:

*Phyllocoptes wisconsinensis* (*eriophyid mite*).—Moderately susceptible with resistance to economic damage by way of high precocity and early harvest characteristics.

*Drosophila suzukii* (*spotted wing drosophila*).—None detected throughout evaluation period.

*Cercospora depazeoides*.—High resistance with no economically important damage observed.

*Alternaria sp*.—High resistance with no economically important damage observed.

Botanical description:

*Type*.—Deciduous shrub with many canes emanating from ground level.

*Hardiness*.—Has been found to tolerate climatic conditions in the Southeastern United States with temperatures in the range of −8° C. to 37° C. Observed to be hardy in USDA Zone 9. This species is documented to be hardy through USDA Zone 4. Hardwood cuttings have been observed to remain viable after up to 12 months of continuous refrigerated storage at 2° C.

*Propagation*.—Nodal hardwood cuttings planted laterally into in-field rows in the plants' intended long-term position. Hardwood cuttings planted in cool soil conditions to encourage root formation before emergence of green shoots. Roots typically initiate after 7-10 days, and newly propagated plants are rooted and well established at 25-40 days.

*Culture*.—Full sun to part-shade, moist but well-drained soil conditions, moderately fertile. Coppiced annually to encourage production of new primocanes.

*Blooming period*.—April to June in the trial range with peak flowering in mid-May.

*Overall plant form*.—Moderately upright (semi-erect), semi-dwarf, vigorous.

*Height and spread*.—Approximately 1.5-2.0 m in height, and approximately 0.75-1.25 m in spread following annual coppicing procedures utilized in commercial cultivation.

*Root system*.—Fibrous, stoloniferous.

*Plant growth habit*.—Clumping tendency of new cane formation, tending not to run more than 10 cm away from the crown as it expands. Mean of 3 primocane-producing canes in the establishment season, mean of 7 primocane-producing canes in the second season, and mean of 10 primocane-producing canes in the third season.

Annual canes:

*Time of new cane formation*.—Mid-to-late January when coppiced in late December in North-Central Florida.

*Length and diameter of new canes*.—Approximately 0.75-1 m in length before initial flower formation. Typical new cane diameter is 1-2.25 cm with an observed range of 0.5-2.75 cm in trials.

*New cane strength*.—Strong and flexible.

*New cane surface*.—Low in waxy surface coating, no pubescence observed on canes at any degree of maturity.

*New cane internodal distance*.—12-14 cm, rarely exceeding 16 cm.

*Predominant distribution of fruiting*.—Primocane bearing with auxiliary branches also bearing on upper third of plant, ranging from 2-6 branches, typically 4 emanating from primocane node junctions, 2 per junction.

*Coloration of internode of new cane*.—PMS376C, HEX #: 76B900 (bright green).

*Anthocyanin coloration of new cane*.—PMS260C, HEX #: 5E1C5F (a medium dark shade of magenta). Anthocyanin coloration extends in a gradient of this color which is moderate at node junction and less deeply concentrated in petiole and rachis.

Auxiliary branches:

*Time of branching*.—Mid-to-late June through July when coppiced in late December in North-Central Florida.

*Length and diameter of auxiliary branches*.—Approximately 0.15-0.25 m in length before flower formation. Typical diameter is 0.7-1 cm with an observed range of 0.5-1.2 cm in trials.

*Auxiliary branch texture*.—Glabrous.

*Auxiliary branch color*.—PMS4515C, HEX #: B5A56F.

*Auxiliary branch internodal distance*.—6-10 cm, rarely exceeding 12 cm.

Leaves:

*Leaf shape*.—Compound leaf and individual leaflets are elliptic in shape. Leaflet apex is acute and the base is cuneate.

*Division*.—Odd-pinnate (5-11 leaflets, usually 7-9 leaflets).

*Leaflet margins*.—Serrulate.

*Size*.—Compound leaves are 20-30 cm in length and 15-25 cm in width. Leaflets are 6-12 cm in length and 2-4.5 cm in width.

*Color*.—Leaf buds are light, bright green (nearest to PMS376C, HEX #: 76B900). The young, unexpanded foliage is also bright green on the lower surface (PMS376C, HEX #: 76B900) and slightly darker on the upper surface (PMS377C, HEX #: 669933). The mature foliage is a slightly darker green (PMS370C, HEX #: 4F8A10) on the upper surface and a slightly muted and lighter green (PMS367C, HEX #: A4D767) on the lower surface. Venation is pale green to nearly white in some cases (a very pale shade of PMS379C, HEX #: DDE56C). Upper and lower leaflet surfaces are very sparsely puberulent to glabrous, with a light waxiness on the upper surface and the lower surface being slightly coarse.

*Leaf petiole length*.—Averaging 1.5 cm.

*Leaf petiole diameter*.—Averaging 2 mm.

*Leaf petiole color*.—PMS370C, HEX #: 4F8A10.
*Rachis length*.—Averaging 20 cm.
*Rachis diameter*.—Averaging 3 mm.
*Rachis texture*.—Glabrous.
*Rachis color*.—PMS370C, HEX #: 4F8A10.

Flowers:

*Inflorescence type*.—Compound flat cyme, which can measure 18-40 cm in diameter (mean of 25 cm) and 6-12 cm in height as measured from the lowest to the highest flower (mean of 10 cm). Individual flowers per primocane cyme were observed to range from approximately 600-1,400 flowers per cyme with between 800-1,200 being most typical. Auxiliary cymes range from 400-900 flowers per cyme, with 500-600 being most typical.
*Flower size*.—4-6 mm in diameter at the corolla. An individual flower has a length of approximately 1.5 mm from ovary base to anther tip.
*Flower structure*.—5 orbicular petals, each about 1 mm across, alternating with the 5 anthers. The sepals are minimal, the style is disk-like and very short (less than approximately 1 mm in length). The stigma is minimal (less than approximately 1 mm in diameter).
*Flower lastingness*.—Typical lastingness of 5-7 days per flower.
*Flower fragrance*.—Strong and sweet fragrance, reminiscent of cake or pastry.
*Flower bud shape*.—Obovate.
*Flower bud diameter and height*.—1-2 mm.
*Flower bud color*.—Light yellow-green (PMS379C, HEX #: DDE56C).
*Petal number*.—5.
*Petal texture on both surfaces*.—Glaucous.
*Petal color on both surfaces*.—Pale cream (a very light shade of PMS600C, HEX #: EEEAB6) to white.
*Pistil number*.—1.
*Ovary color*.—Light yellow-green (PMS379C, HEX #: DDE56C).
*Stamen number*.—5.
*Stamen length*.—2-3 mm.
*Anther length*.—Averaging 0.7 mm.
*Anther width*.—Averaging 0.3 mm.
*Anther color*.—Light yellow (PMS393C, HEX #: EDEB8F).
*Filament color*.—Pale cream (a very light shade of PMS600C, HEX #: EEEAB6) to white.
*Sepal shape*.—Ovate.
*Sepal length*.—Averaging 0.6 mm.
*Sepal width*.—Averaging 0.3 mm.
*Calyx lobe number*.—5.
*Pollen color*.—Light yellow (PMS393C, HEX #: EDEB8F).
*Pollen production per flower*.—Moderate.

Fruit:

*Ripe fruit color*.—Very dark purple-black surface, essentially black with a glossy sheen of red-purple in full daylight. Equally dark flesh and intensely purple-red juice at its natural pH of 4.8 to 5.0. No Pantone or HEX #color values adequately reflect the colors of the ripe fruit and juice, but they are most similar to PMS229C, HEX #: 6A1D44 before fully ripe.
*Fruit shape*.—Globose.
*Fruit presence*.—June through August. Earliest observed harvest date June 30, typically July 4 through July 7 for second-and third-season plants. Earliest observed harvest for establishment year plants is July 20, typically July 30 through August 30 when hardwood cuttings were planted directly in rows in early December. A last harvest date of July 30 was used annually in commercial production trials for second-and third-season plants and August 30 for establishment year plants. Auxiliary cymes of second-and third-year plants continue to ripen through late August in a typical season.
*Fruit size*.—5-7 mm in diameter and equal in height.
*Fruit weight*.—Typically 100-130 mg per individual drupe.
*Fruit yield*.—Per plant yields observed under agricultural practices utilized were observed at a range of 350-556 g per plant in the establishment year through August 30; 426-1,030 g per plant in the second year; and 633-1,584 g per plant in the third year through July 30.
*Seeds*.—3-5 seeds (typically 4 seeds, with 5 seeds being more common than 3 seeds). Seeds are tan in color (PMS134C, HEX #: F8D583) and approximately 1.5 mm in width and approximately 2 mm in length, and 0.8 mm in height. Seed shape is ovate and slightly scalloped.

Chemical characteristics of pressed juice:

*Samples in table* 1.—Sample "D (2024)" is of the juice from the berries of the original seedling in its third season, harvested Jul. 7, 2024. Sample "E (2024)" is of the juice from the berries of the first asexually reproduced plants from the original seedling, in their second season, harvested Jul. 7, 2024. Sample "F (2024)" is of the juice from the berries of the second group of asexually reproduced plants, harvested Jul. 7, 2024, where the propagation material was taken from the plants corresponding to the "E (2024)" group. Sample "A (2024)" is of the juice from the berries of the original seedling harvested in its first season on Aug. 23, 2022, at 11 months from sowing.
*Sweetness/soluble solids in ° brix*.—See Table 1 below.

TABLE 1

| Sample (Year Observed) | Sweetness/Soluble Solids (°brix) |
|---|---|
| D (2024) | 10.9 |
| E (2024) | 11.4 |
| F (2024) | 12.4 |

Titratable acidity as % citric acid: See Table 2 below.

TABLE 2

| Sample (Year Observed) | Titratable Acidity (% Citric Acid) |
|---|---|
| D (2024) | 0.54% |
| E (2024) | 0.47% |
| F (2024) | 0.54% |

Total anthocyanins (TAC) per HPLC as Cy-3GE mg/g: See Table 3 below.

TABLE 3

| Sample (Year Observed) | TAC (Cy-3GE mg/g) |
|---|---|
| A (2022) | 11.73 |

Total anthocyanins (TAC) per HPLC as grams anthocyanin/L: See Table 4 below.

TABLE 4

| Sample (Year Observed) | Total Anthocyanins (g/L) |
|---|---|
| D (2024) | 12.52 |
| E (2024) | 13.12 |
| F (2024) | 15.25 |

Cyanidin 3-(6"-(E)-p-coumarylsambubioside) 5-glucoside per HPLC as grams $C_{41}H_{45}O_{22}^{+}$/L: See Table 5 below.

TABLE 5

| Sample (Year Observed) | Cyanidin 3-(6"-(E)-p-coumarylsambubioside) 5-glucoside (g/L) | % of TAC |
|---|---|---|
| D (2024) | 9.72 | 77.64% |
| E (2024) | 9.70 | 73.93% |
| F (2024) | 11.07 | 72.59% |

What is claimed is:

1. A new and distinct *Sambucus* plant named 'Æ-1' as illustrated and described herein.

* * * * *